United States Patent
Shovers et al.

[11] 3,952,414
[45] Apr. 27, 1976

[54] BONE IMPLANT

[76] Inventors: Aaron H. Shovers, 2704 Del Amo Blvd., Lakewood, Calif. 90712; Norman M. Pokras, 4448 Village Road, Long Beach, Calif. 90808

[22] Filed: Oct. 29, 1974

[21] Appl. No.: 518,476

[52] U.S. Cl. ............................................. 32/10 A
[51] Int. Cl.² ......................................... A61C 13/00
[58] Field of Search ........................... 32/10 A, 15

[56] References Cited
UNITED STATES PATENTS

| | | | |
|---|---|---|---|
| 2,210,424 | 8/1940 | Morrison | 32/10 A |
| 3,579,831 | 5/1971 | Stevens | 32/10 A |
| 3,589,011 | 6/1971 | Sneer | 32/10 A |
| 3,715,331 | 2/1973 | Molnar | 32/15 |
| 3,851,393 | 12/1974 | Weiss | 32/10 A |

FOREIGN PATENTS OR APPLICATIONS

| | | | |
|---|---|---|---|
| 978,502 | 4/1951 | France | 32/10 A |

*Primary Examiner*—Robert Peshock
*Attorney, Agent, or Firm*—Fulwider, Patton, Rieber, Lee & Utecht

[57] ABSTRACT

There is disclosed a method for the prevention of osteitis and for the prevention of atrophy of alveolar bone, which comprises embedding an implant into a boney cavity such as a cystic cavity or an alveolus after a tooth extraction. The implant is a body of a tissue-compatible material and has a smooth unbroken exterior surface defining a bulbous, gibbous shape which generally follows the contour of the cavity. It is important that the material of the implant be inert to the body. The implant can be employed in cavities which are too large to permit the normal primary and secondary healing processes to fill the cavity with trabecular bone tissue. In the preferred embodiment, the invention is applied to the prevention of atrophy of alveolar bone following the extraction of a tooth. In this application, the implant is placed in the socket following removal of the tooth. The size and placement of the implant are sufficient to locate the occlusal end of the implant approximately 3 to 4 mm. beneath the height of the boney tissue. When the implant is positioned at this depth, the normal healing processes are adequate to entirely surround the implant with trabecular bone and to form an occlusal layer of boney tissue above the implant. This reinforces the alveolar bone similar to steel reinforced concrete. The surrounding alveolar process retains its original strength and shape and atrophy is prevented.

20 Claims, 12 Drawing Figures

FIG.1
FIG.2
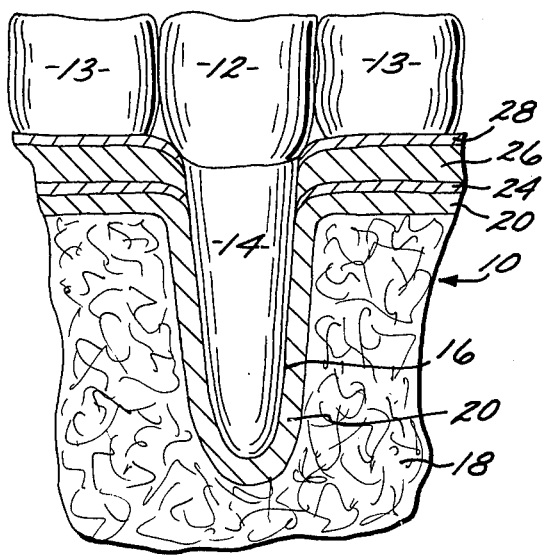
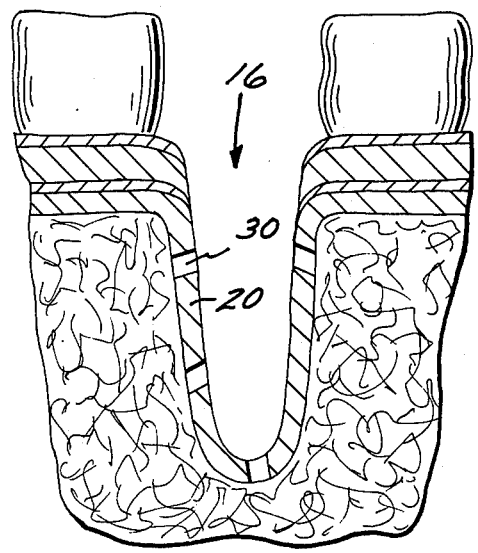
FIG.3
FIG.4
FIG.6
FIG.5
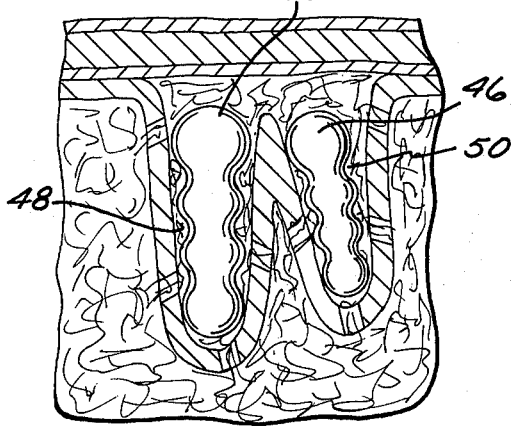
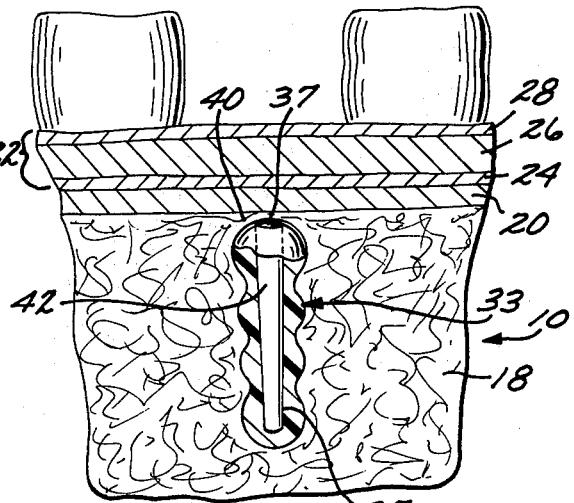
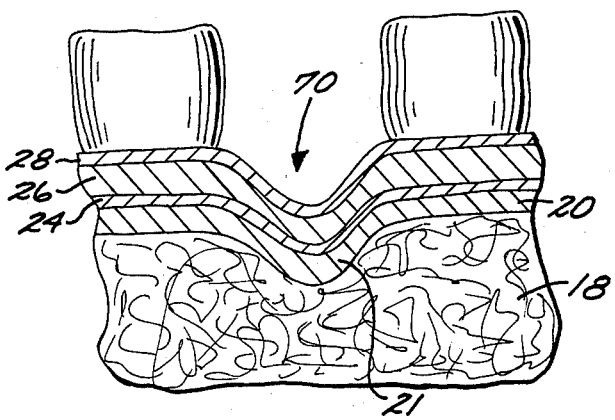

BONE IMPLANT

BACKGROUND OF THE INVENTION

This invention relates to a bone implant and, in particular, relates to an implant for alveolar bone.

DESCRIPTION OF THE PRIOR ART

Certain surgical operations, particularly in the field of dentistry, result in cavities within boney tissue. These operations can be the removal of cysts or tumors from bones, forming a cystic cavity or can be the removal of impacted wisdom teeth and the like, resulting in a cavity in the alveolar bone, i.e, an alveolus. Commonly, the remaining cavity is surrounded by cortical bone. The normal healing processes of the body are operative to fill these cavities with trabecular tissue by first forming a blood clot in the cavity, establishing circulation therein and then forming progressive layers of tissue inwardly from the exterior surfaces of the cavity. When these cavities are large, the required circulation can not be established in the entire cavity and the blood clot undergoes lysis frequently resulting in osteitis or in "dry sockets" of alveolar bone.

After extraction of a tooth, even if the healing processes of the body function perfectly, the healed alveolus quickly resorbs with an occlusal indentation and unesthetic, sharp ridges which are ill-suited to support dental prosthetic devices such as bridgework and partials. Stress concentrations resulting from multiple extractions promote atrophy of the alveolar bone, often resulting in complete inability of the remaining bone to support dental partial and full dentures and, in general weakening the jawbone, and rendering it more prone to fracturing.

A number of prior investigators have suggested various implants which are suggested as useful for positioning in the socket remaining after extraction of a tooth. Most of these implants are intended for use as anchors for dental prosthetic devices and, accordingly, have a large occlusal surface exposed to the oral cavity. These implants are not entirely satisfactory because of their failure to be isolated from the oral cavity. The gingival tissue often does not develop about the implants sufficiently to seal the tissues against bacterial infiltration. Accordingly, the initial healing process about the implant is often disrupted by infections from the oral cavity. Even when successful healing is accomplished, subsequent infection of the alveolar bone can occur, resulting in discomfort and, frequently, requiring extraction of the implant. Another common failing of the various alveolar implants has been the failure to recognize the need for continuous circulation within the blood clot and tissue that is formed about the implant. Consequently, many of the alveolar implants have employed sharp-edged surfaces or discontinuous exterior surfaces which form crevices and dead pockets within the alveolar cavity when the implant is inserted. Typical of these is the device disclosed in U.S. Pat. No. 3,576,074 in which a dental endosseous implant is disclosed as useful for complete embedding in the alveolar socket. The disclosed implant is, however, not well suited for the intended use since it has a large, exposed pocket which would prevent adequate circulation and many sharp, planar junctions that are not physiologically acceptable. Particularly critical in this regard is the upper flat planar surface of the patented implant which will prevent the growth of an overlying, occlusal layer of bone. The implant is used as an anchor for an artificial crown by parting the overlying gingival tissue, exposing the entire upper area of the device to the oral cavity. This too, is not physiologically acceptable because of the excessive area that is exposed to the oral cavity, increasing the likelihood of infection.

BRIEF STATEMENT OF THE INVENTION

The invention comprises a method for the prevention of osteitis by embedding into a cavity of a bone an implant having a bulbous shape to fill a major portion of the cavity and having a continuous exterior surface, free of crevices, and characterized by a gibbous or nodular surface. The implant has bulbous ends and is entirely physiologically compatible. The implant is embedded entirely within the surrounding bone. When the method is applied to implants in the alveolus, the implant is positioned to a depth of about 2 to 5, preferably 3 to 4 millimeters beneath the level of the surface bone, sufficient to permit occlusal growth over the occlusal, bulbous end of the implant whereby the implant in the alveolus is totally enclosed by boney tissue developed during the healing process.

The implant employed in the device has a continuous unbroken surface. The implant can be a solid-form body or can have a totally enclosed central or longitudinal cavity which can be aligned with the cavity in the alveolus to provide for subsequent attachment of dental prosthetic devices. The exterior surface of the implant is continuous and is characterized by a gibbous or nodular surface to provide means for lodging and securing the implant within the alveolar cavity. The general shape of the implant is bulbous and the curvilinear irregularities of its continuous surface can be in a geometric pattern such as a surface of trochoidal revolution or entirely irregular in form.

When the implant is a solid form body it can be formed of inert materials such as carbon, graphite, porcelain, titanium, gold, vitallium, tantalum, synthetic resins such as Teflon, Ivalon and the like. The implant can also be formed of calcium sulfate, e.g., plaster of Paris which can be reinforced with a suitable internal structure and thereby serve as a supply of calcium for bone growth. To preclude the possibility that resorption of calcium from the implant body would expose a central cavity therein, only solid form implants should be formed with a body of calcium sulfate. Any of the implants formed of inert material could, of course, bear a calcium sulfate containing outer layer or coating.

BRIEF DESCRIPTION OF THE DRAWINGS

The invention will be described by reference to the drawings of which:

FIG. 1 illustrates the alveolar process with teeth in place;

FIG. 2 illustrates the cavity in the alveolar bone which results from a tooth extraction;

FIG. 3 illustrates the placement of the implant of the invention;

FIG. 4 illustrates the alveolus after completion of the healing process;

FIG. 5 illustrates the healing of an alveolus which results when no implant is employed;

FIG. 6 illustrates application of the invention to a molar extraction;

DESCRIPTION OF PREFERRED EMBODIMENT

Figure 7:
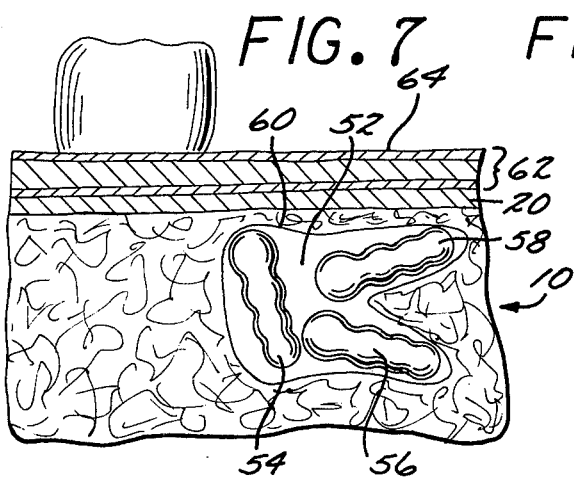
FIG. 7 illustrates application of the invention for prevention of dry socket following extraction of an impacted tooth.

Referring now to FIG. 1 there is illustrated an alveolar portion of a human maxilla or mandible. Positioned in the alveolar bone 10 is a tooth such as a cuspid 12 having a root 14 that extends into and is supported by a root cavity 16, the alveolus. On either side of this tooth are adjacent teeth 13. The structure surrounding the root cavity 16 includes the canellous bone 18 separated from the cavity by the layer 20 of the cortical bone. The gingival tissue overlying the alveolar bone comprises the periosteal membrane 24, submucosa 26 and mucosa or epithelium 28.

FIG. 2 illustrates the alveolus following a normal extraction and without any destruction of the alveolar bone. This extraction exposes the entire root cavity 16. In the preferred embodiment of the invention, the lamina dura 20 is pierced with one or more apertures 30 by drilling, preferably with a round burr of approximately No. 10 size. The apertures through this cortical bone are made to promote hemorrhaging from the cancellous bone and thereby improve the healing process.

The cavity 16 is partially filled by the placement of the implant 32 into the cavity in the manner shown in FIG. 3. The implant is firmly seated in the cavity and secured therein by a gentle tap to preclude its expulsion from the cavity. The implant 32 is a solid-form body of a material which is compatible with body tissue. Various materials which can be employed such as porcelain, carbon, graphite, vitallium, tantalum, platinum, titanium, gold, and synthetic plastics such as polyethylene, polypropylene, polyvinyl alcohol, Teflon, polymethylmethacrylate, etc.

When the implant is solid form such as 32, another suitable metarial is calcium sulfate, e.g., plaster of Paris, that is molded to the desired shape. This material is not inert to the body, but is compatible therewith and, in fact, functions as a supply of calcium which is absorbed locally and utlized in the new bone growth at this site of healing, thereby accelerating the development of the surrounding bone tissue. As described hereinafter with regard to FIGS. 10 and 11, the implant can also bear internal reinforcement. The calcium source could also be provided, with a hollow core body of an inert material by surface coating the inert body with plaster of Paris.

The general configuration of the implant 32 is bulbous with a smooth and continuous, i.e., unbroken, exterior surface. The surface can be gibbous or nodular and characterized by a plurality of curvalinear protuberances 34 which can, if desired, extend entirely about the periphery of the body in the manner illustrated by gibbous portion 36. Various configurations for this body can be employed such as regular protuberances as would be formed in a body of trochoidal revolution or irregular bands.

The major dimension of the body in its placement in the cavity 16 is such that its occlusal end is positioned a slight distance beneath surrounding level of the boney height 23. Typically the occlusal end of body 32 should be from 2 to about 5, preferably from 3 to about 4 millimeters beneath the level of this boney height. As apparent from FIG. 3, the implant 32 substantially fills cavity 16 but does not present any crevices or dead spaces within cavity 16 that would interfere with free circulation of body fluids through the cavity 16. Accordingly, the healing process can proceed by the formation of a blood clot in the primary stage of healing and the orderly and progressive formation of layers of preosteum from the lamina dura layer inwardly to form about the exterior surface of implant 32, securing the implant in cavity 16, after which mature bone will form.

The positioning of the occlusal end of body 32 beneath the boney height insures occlusal growth of the alveolar bone and gingival tissue over implant 32. The result of this healing process is illustrated in FIG. 4 where the gingival layer 22 of the tissue, consisting of the periosteal layer 24, submucosa layer 26 and epithelium layer 28, can be seen to overlie the alveolus without any surface indentation or ridges. The alveolar bone 10 is shown with travecular tissue 38 which entirely surrounds implant 33. This trabecular tissue can be seen to have also formed an occlusal layer 40 over the occlusal end of implant 32. Cortical bone 20 also covers this area, forming a firm support for the overlying gingival layers 22.

The implant 33 shown in FIG. 4 is illustrated as having a central and totally enclosed cavity 42. This is an optional variation in construction of the implant and can be employed when it is desired or expected to employ the implant 33 as an anchor for dental porsthetic devices. This central cavity 42 can subsequently be employed by piercing the overlying gingival tissue layer 22 and drilling through the occlusal layers 20 and 40 of bone. When so employed, the central cavity 42 can be useful to receive a pin to help anchor a prosthetic device such as a crown, bridge or partial or full dentures as described in greater detail hereinafter with regard to FIG. 8.

When the implant has a central cavity, it is preferred to fill this cavity with a radio-opaque substance 35 such as barium sulfate and the like. Subsequent examination by X-rays will then precisely locate the central cavity and greatly assist the dentist in piercing this cavity. It is also desirable to code the exterior end of the implant with in indicium 37 such as a circle or dot which is in alignment with the cavity and which thereby indicates the location of the cavity to the dentist.

As previously mentioned, the alveolus remaining after a tooth extraction will not heal without leaving an unesthetic occlusal indentation with sharp edges which are ill-suited to support dental prosthetic devices. Stress concentrations on the healed structures promote atrophy of the alveolar bone and thereby increase the depth of such surface indentation. FIG. 5 illustrates a cross-section of a healed alveolar bone when no implant is placed in the alveolus. As illustrated, the jaw is characterized by a very pronounced occlusal indentation 70 which overlies the area of the alveolus formed by extraction of the tooth, e.g., alveolus 16 illustrated in FIG. 2. The healing process results in the growth of the cortical layer of bone 20 entirely across the alveolus but with a very pronounced indentation 21. Concurrent with the development of this occlusal layer of cortical bone 20 is the disappearance of the cortical bone that formerly lined the alveolus and the formation of trabecular bone 18. The overlying layers of tissue such as the periosteal membrane 24, submucosa 26, and mucosa or epithelium 28 follows the contour of the cortical bone with the same indentation 21 formed therein resulting in the very pronounced occlusal indentation 70. With aging and stress application on the alveolar bone, atrophy will unavoidably occur with resorbtion of the boney tissue such that occlusal indentation 70 becomes progressively more pronounced and the alveolar bone becomes progressively weaker and more subject to fracture. Also the adjoining teeth are endangered and lost as this resorption progresses. The implants of this invention avoid this condition in the manner previously described.

Referring now to FIG. 6, there is illustrated the employment of a plurality of implants 44 and 46 which can be used to fill, substantially, the diverse legs 48 and 50 of the root cavity remaining after extraction of a molar. Preferably, each of the legs is filled with one of the implants although a plurality of implants could be used in a single leg if desired. As illustrated, the implants can be supplied in varied sizes and shapes to provide a progressive or incremental variation in size and shape that would permit preselection of an implant to closely conform to the particular alveolar cavity.

FIG. 7 illustrates the application of the invention to the cavity remaining in the alveolar bone 10 after extraction of an impacted tooth such as an impacted wisdom tooth. The extraction of the impacted tooth leaves a cavity 52 which is totally enclosed in the alveolar bone. This cavity is sufficiently large that, frequently, lysis of the blood clot, which is formed during the normal healing process, occurs resulting in necrosis. This is commonly referred to as "dry socket"; and the lysis of the blood clot results in delayed healing following 10 to 14 days of extreme pain. This invention obviates the aforedescribed difficulty by limiting the volume of the alveolus. This is achieved by embedding one or more of the endossious implants 54-58 in the cavity to fill a substantial void of the cavity and reduce the volume in which circulation must be established for development of the necessary trabecular boney tissue. After the implants have been positioned and secured in the desired locations within cavity 52, the normal healing process is permitted to proceed, resulting in the formation of an occlusal layer 60 of the alveolus which is overlaid by the layers of gingival tissue 62 and in the formation of an occlusal surface 64 which is free of depressions or ridges. Thus the sub-boney implants act to reinforce and brace the bone to secure it against atrophy.

Figure 8:
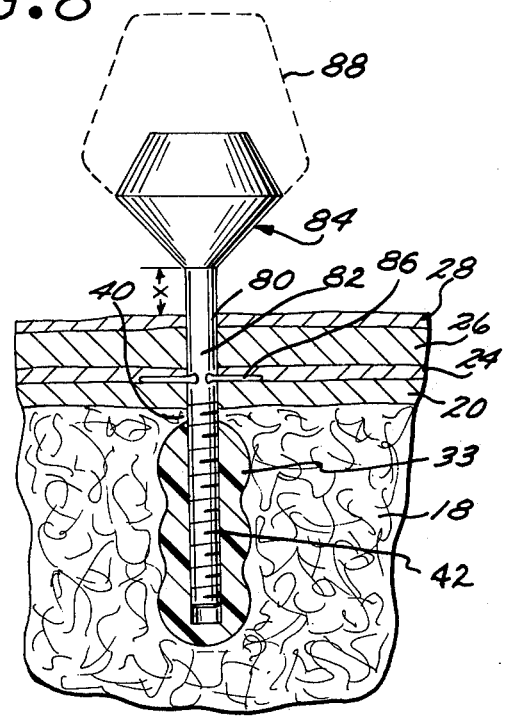
FIG. 8 illustrates the proper use of the implant as an anchor for a prosthetic device.

As previously mentioned, the implants of this invention can desirably be used as supporting anchors for pins and the like that can be used to support prosthetic devices such as crowns, bridges or partial or full dentures. FIG. 8 illustrates the preferred mannner in which prosthetic devices can be anchored to an alveolar bone that bears an implant 33. As illustrated, the portion of the alveolar bone illustrated in FIG. 4 has progressed to where substantially complete healing has resulted in disappearance of the cortical bone surrounding the former alveolus, commonly achieved after 6 months to 1 year following implantation of the implant 33. The dentist has opened the gingival tissue comprising the epithelium 28, submucosa 26 and the periosteum 24. Then with a narrow diameter drill, e.g., one having a diameter of from 2 to about 5 millimeters, a bore 80 is continued through the layers of cortical bone 20 and trabecular bone 40 which overlies the former alveolus. The bore is aligned by the dentist to enter implant 33 at approximately the position of the indicium 37 (see FIG. 4) carried on the bulbous upper occlusal end of implant 33. The bore thereby opens the internal cavity 42 and, when this cavity is packed with a radio-opaque material, removes it from the cavity rendering it suitable for reception of the slender metallic rod 82 of the implant support 84. Preferably the lower end of rod 82 bears external threads which mate with internal threads of cavity 42 which are preferably preformed. Rod 82 also could be of noncircular cross section or bear a key on its outer surface and cavity 35 is of mating dimensions so that the rod will be secured in cavity 35 firmly and resist turning about its axis. The rod can be secured in place by any suitable means, e.g., conventional dental cement or mechanical lock means, screw, detents and the like. Lateral support arms 86 which can be loops of rod material seat upon the bone to aid in preventing tilt.

The implant support 84 carried on the occlusal end of rod 82 can be of a suitable shape and size to permit its use for anchoring a prosthetic device such as artificial crown or socket to anchor a partial or denture 88. Preferably, the head of the support 84, as well as any prosthetic device carried thereon, is supported a distance above the epithelium so that the entire surrounding gingival surface is self cleaning with oral lavage. Desirably, this distance, $x$, should be about 1 to about 3, preferably from 1 to about 2 millimeters.

Figure 9:
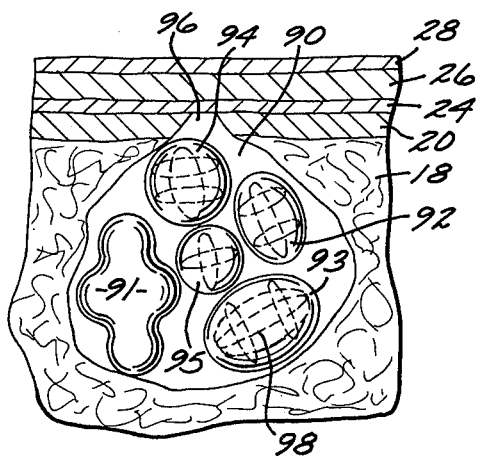
FIG. 9 illustrates use of the invention in a cystic cavity.

The invention is also useful, as previously pointed out, for the prevention of osteitis of cystic cavity. Application of the invention to this treatment is illustrated in FIG. 9 where a cystic cavity 90 is formed in the surrounding trabecular bone 18 following the removal of a cyst and the like. Cavity 90 is filled with one or more of the implant devices 91-95 which are placed in the cavity through the aperture that is formed during the cystectomy. The overlying tissue such as the overlying gingival tissue in the oral cavity comprising epithelium 28, submucosa 26 and periosteum 24 is sutured over aperture 96. The normal healing process will then be promoted and accelerated due to the implants limiting the amount of blood clot which must be organized and eventually calcified, resulting in complete filling of cavity 90 by the orderly growth of trabecular bone.

As illustrated, the implants employed in filling a cystic cavity can bear a plurality of shapes and sizes such as the generally spherical shape of implant 94 or the ellipsoidal shapes of implants 92 and 93 or the irregular nodular shape of implant 91. Also, if desired, the implants can bear internal and completely covered reinforcement means 98 which can be in the form of members that are innerconnected to form a supporting cage structure.

Figure 10:
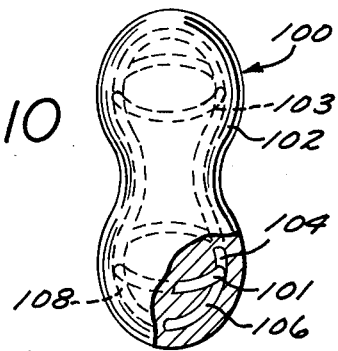
FIG. 10 illustrates a reinforced solid form implant.

FIG. 10 illustrates a suitable implant 100 which is formed of solid form material 102 that can be any of the aforementioned body-compatible materials. The implant can have an internal supporting frame work 104 defined by a plurality of longitudinal members 106 and 108 which can, if desired, be sides of a continuous loop and a plurality of transverse members 101 and 103. The material 102 of the implant entirely surrounds the reinforcement means 104 so that the resultant body is solid form.

Figure 11:
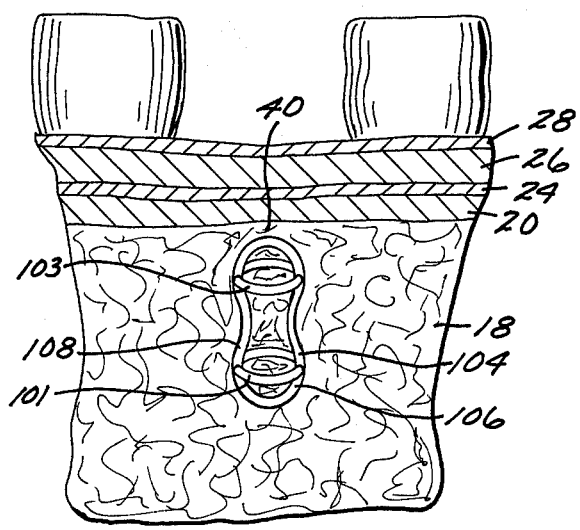
FIG. 11 illustrates a healed alveolus that results when a plaster of Paris body of the FIG. 10 construction is used.

The implant 100 described and illustrated in FIG. 10 can be formed with solid calcium sulfate, e.g., plaster of Paris or a material to promote bone healing. As previously mentioned, this comprises a special embodiment of the solid form implant in that the implant serves as a source of calcium to promote and accelerate the growth of trabecular and cortical bone in a cystic cavity or alveolus. FIG. 11 illustrates a healed portion of an alveolar bone in which the implant such as 100 of FIG. 10 has been utilized to prevent an occlusal indentation, such as 70 illustrated in FIG. 5. This results in the growth of the cortical bone 20 as an occlusal layer, entirely overlying gingival tissue of the periosteum 24, submucosa 26, epithelium 28 and an overlying layer 40 of trabecular bone. Located in the trabecular bone 18 which has formed in the alveolus, is the reinforcement 104 in the form of a wire cage. The entire body, or, at least a substantial portion thereof, of implant 100 has been absorbed by the body tissue and utilized as a source of calcium for the development of the boney tissue in an alveolus. This results in an entirely embedded reinforcement 104 within the alveolar bone as illustrated in FIG. 11. The material used as the members 106, 108, 101 and 103 should be body-compatible and can be any of the aforementioned inert materials.

Figure 12:
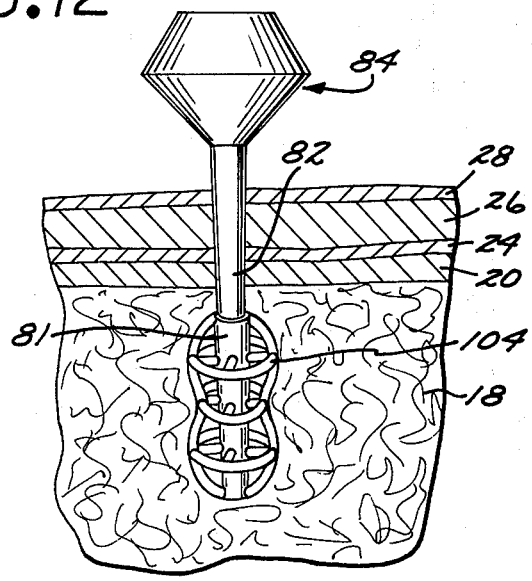
FIG. 12 illustrates variation of the implant shown in FIG. 10.

FIG. 12 shows a variation of this framework totally enclosed in bone 18 and covered by cortical bone 20, periosteum 24, submucosa 26 and epithelium 28 which carries a hollow form body 81 to enclose pin 82 and implant support 84. This framework 104 could also serve to support a future prosthetic device such as 88 shown in FIG. 4. Hollow form body 81 is, of course, totally enclosed when placed in the body and is subsequently pierced in the manner described with regard to FIG. 4.

The invention has been described with reference to the presently preferred and illustrated modes of embodiment. It is not intended that the invention be unduly limited by this disclosure of preferred embodiments. Instead, it is intended that the invention be defined by the elements, steps and their obvious equivalents, set forth in the following claims.

What is claimed is:

1. A method for the prevention of osteitis and the promotion of healing in the cavity of a bone such as a cystic cavity and the like which comprises:
   forming an implant formed of a tissue-compatible material having contour and dimensions approximating said cavity and having a continuous, unbroken bulbous and gibbous exterior surface free of crevices including generally spherical ends and at least one waist section of reduced cross section intermediate its length;
   positioning said implant within said cavity totally within the confines of the surrounding boney tissue and at least 2 to 5 millimeters beneath the surrounding layer of boney tissue, sufficient to permit growth of said boney tissue thereover; and
   permitting said bone to heal by primary and secondary healing to form trabecular tissue totally about said implant and fill the voids remaining between said implant and surrounding bone.

2. A method for the prevention of atrophy of alveolar bone folowing the extraction of a tooth which comprises:
   forming an elongated implant of a body of a tissue-compatible material having a bulbous exterior defined by a continuous, unbroken, and gibbous exterior surface free of crevices including generally spherical ends and at least one waist section of reduced cross section intermediate its length;
   positioning said implant into the root socket formed by said extraction with its occlusal end at an occlusal distance of from two to about five millimeters beneath the height of the alveolar bone, sufficient to permit occlusal growth of boney tissue over the generally spherical occlusal end of said implant; and
   permitting alveolar boney tissue to form about said implant and enclose said cavity.

3. The method of claim 2 including the step of puncturing the lamina dura surrounding said cavity with at least one aperture to enhance hemorrhaging into said cavity.

4. The method of claim 2 wherein said implant is a solid form body.

5. The method of claim 4 wherein said implant is formed of solid plaster of Paris with an internal metallic reinforcement.

6. The method of claim 2 wherein said implant has a totally enclosed central, longitudinal cavity.

7. The method of claim 6 wherein said cavity is filled with a radio-opaque substance.

8. The method of claim 2 wherein said implant has an irregular shape.

9. The method of claim 2 wherein said implant has a nodular exterior surface.

10. The method of claim 2 wherein said implant has an exterior shape of a trochoidal surface of revolution.

11. The method of claim 6 including the step of drilling a bore having a diameter from 2 to about 5 millimeters through said occlusal layer of the alveolar bone and into the aforesaid central cavity to expose a socket in the implant suitable for retention of a dental prosthetic device.

12. The method of claim 11 including the step of positioning an implant support having a support head and a support rod having a diameter to fit said bore with the support rod in said socket supporting said head above said occlusal layer and securing thereto a dental prosthetic device a distance of from 1 to about 3 millimeters above the epithelium and sufficient to permit cleaning by oral lavage.

13. A dental endosseous implant that comprises a body of tissue-compatible material having a non-wedge shape with a continuous and smoothly rounded exterior surface characterized by gibbous and nodular protuberances with generally spherical ends and at least one waist section intermediate its length for embedding totally within a bone cavity and at least 2 to about 5 millimeters beneath the surrounding layer of boney tissue, sufficient to permit growth of said boney tissue thereover.

14. The implant of claim 13 wherein said body is irregular in shape.

15. The implant of claim 13 wherein said body is defined by a trochoidal surface of revolution.

16. The implant of claim 13 wherein said body is solid form.

17. The implant of claim 16 wherein said body is formed of solid plaster of Paris with an internal metallic reinforcement.

18. The implant of claim 13 wherein said body has a totally enclosed central longitudinal cavity.

19. The implant of claim 18 wherein said cavity is filled with a radio-opaque substance.

20. The implant of claim 18 wherein an end of said body bears an indicium on its exterior surface to indicate the location of said cavity.

\* \* \* \* \*